United States Patent
Woods et al.

(10) Patent No.: US 7,248,926 B2
(45) Date of Patent: Jul. 24, 2007

(54) STATUS INDICATOR FOR IMPLANTABLE SYSTEMS

(75) Inventors: Carla Mann Woods, Beverly Hills, CA (US); Michael A Faltys, Northridge, CA (US); Lee F Hartley, Calgary (CA)

(73) Assignee: Advanced Bionics Corporation, Valencia, CA (US)

( * ) Notice: Subject to any disclaimer, the term of this patent is extended or adjusted under 35 U.S.C. 154(b) by 488 days.

(21) Appl. No.: 10/651,652

(22) Filed: Aug. 29, 2003

(65) Prior Publication Data

US 2004/0044383 A1    Mar. 4, 2004

Related U.S. Application Data

(66) Substitute for application No. 60/407,259, filed on Aug. 30, 2002.

(51) Int. Cl.
*A61N 1/08*      (2006.01)
*A61N 1/36*      (2006.01)

(52) U.S. Cl. ................... 607/29; 607/55; 607/56; 607/57; 607/33

(58) Field of Classification Search ............ 607/55–57, 607/29, 61, 33; 128/903
See application file for complete search history.

(56) References Cited

U.S. PATENT DOCUMENTS

| | | |
|---|---|---|
| 3,902,478 A | 9/1975 | Konopasek et al. |
| 3,953,848 A | 4/1976 | Dillman et al. |
| 4,522,209 A | 6/1985 | Patrick et al. |
| 4,532,930 A | 8/1985 | Crosby et al. |
| 4,675,656 A | 6/1987 | Narcisse |
| 4,918,745 A | 4/1990 | Hutchison |
| 4,952,864 A | 8/1990 | Pless et al. |
| 5,024,224 A | 6/1991 | Engebretson |
| 5,266,919 A | 11/1993 | Cook et al. |
| 5,344,387 A | 9/1994 | Lupin |
| 5,370,668 A | 12/1994 | Shelton et al. |
| 5,402,070 A | 3/1995 | Shelton et al. |
| 5,404,877 A | 4/1995 | Nolan et al. |
| 5,584,869 A | 12/1996 | Heck et al. |
| 5,603,726 A | 2/1997 | Schulman et al. |
| 5,690,693 A | 11/1997 | Wang et al. |
| 5,702,431 A | 12/1997 | Wang et al. |
| 5,769,877 A | 6/1998 | Barreras, Sr. |
| 5,824,022 A | 10/1998 | Zilberman et al. |
| 5,876,425 A * | 3/1999 | Gord et al. .................. 607/56 |
| 5,941,905 A | 8/1999 | Single |
| 6,002,966 A | 12/1999 | Loeb et al. |

(Continued)

FOREIGN PATENT DOCUMENTS

EP      0706407 B1      9/1997

*Primary Examiner*—Carl Layno
*Assistant Examiner*—Tammie K Heller
(74) *Attorney, Agent, or Firm*—Bryant R. Gold

(57) ABSTRACT

A status indicator is provided for use with a medical device that employs a power transmitting coil. In one embodiment, the status indicator comprises a receiving coil and feedback element. The feedback element, such as a light emitting diode (LED) or liquid crystal display (LCD), is electrically coupled to the receiving coil. In another embodiment a status indicator is incorporated into the medical device, which status indicator comprises a feedback element and electronic circuitry for detecting device function and program selection. The circuitry and feedback element are incorporated into the medical device such as on the earhook of a behind-the-ear (BTE) hearing device.

6 Claims, 2 Drawing Sheets

U.S. PATENT DOCUMENTS

| | | |
|---|---|---|
| 6,157,861 A | 12/2000 | Faltys et al. |
| 6,185,461 B1 | 2/2001 | Er |
| 6,205,359 B1 * | 3/2001 | Boveja ........................ 607/45 |
| 6,671,552 B2 | 12/2003 | Merritt et al. |
| 6,681,135 B1 | 1/2004 | Davis et al. |
| 6,788,790 B1 | 9/2004 | Leysieffer |
| 2003/0114899 A1 | 6/2003 | Woods et al. |

\* cited by examiner

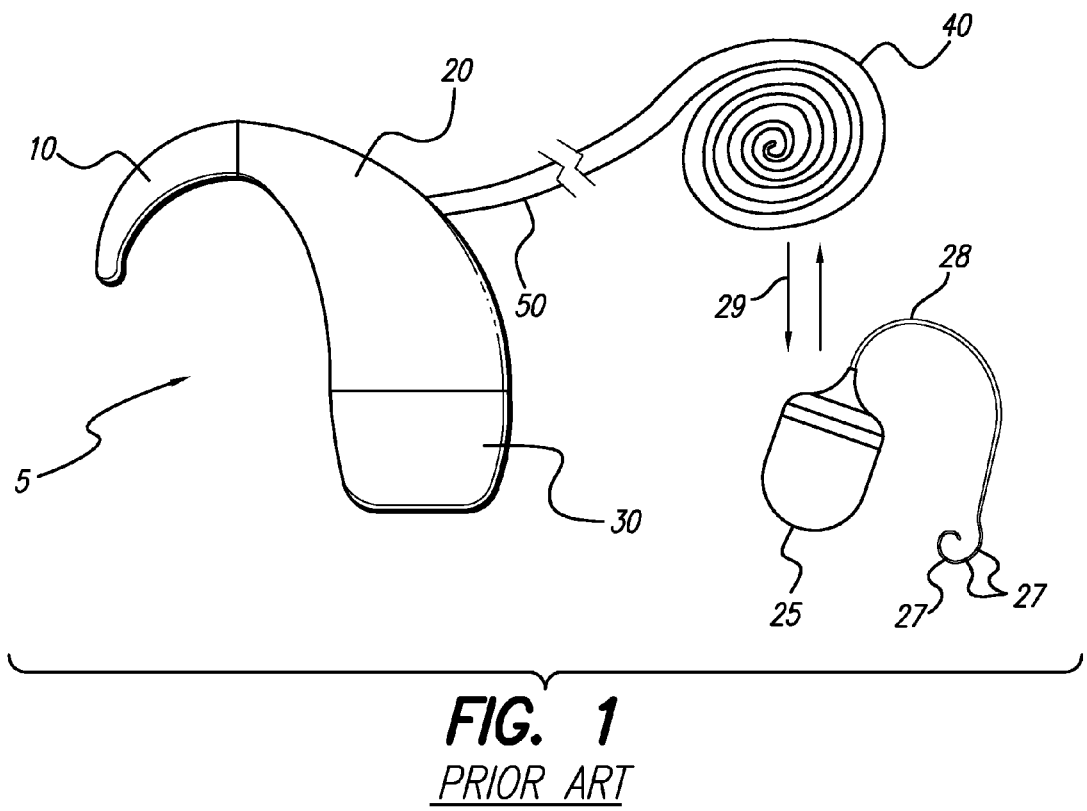
FIG. 1
PRIOR ART
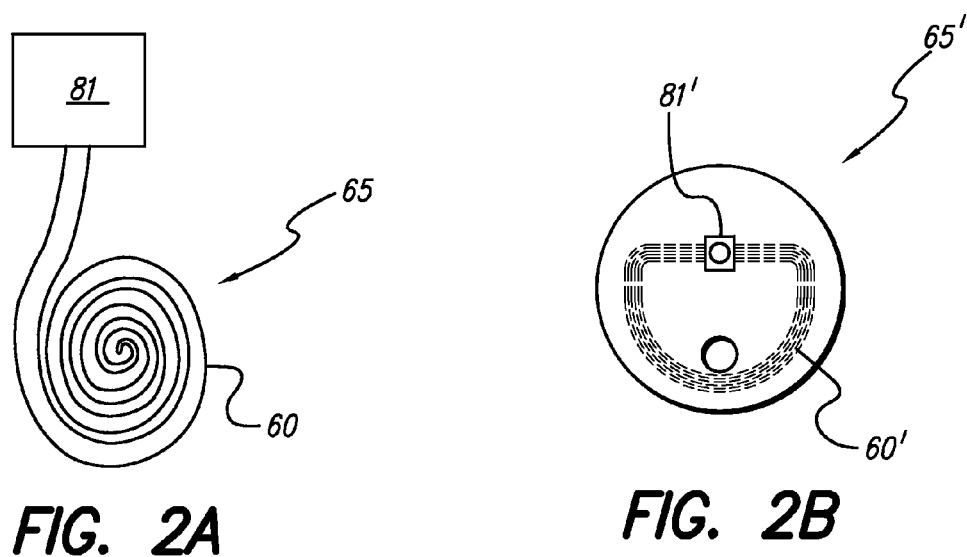
FIG. 2A　　　FIG. 2B

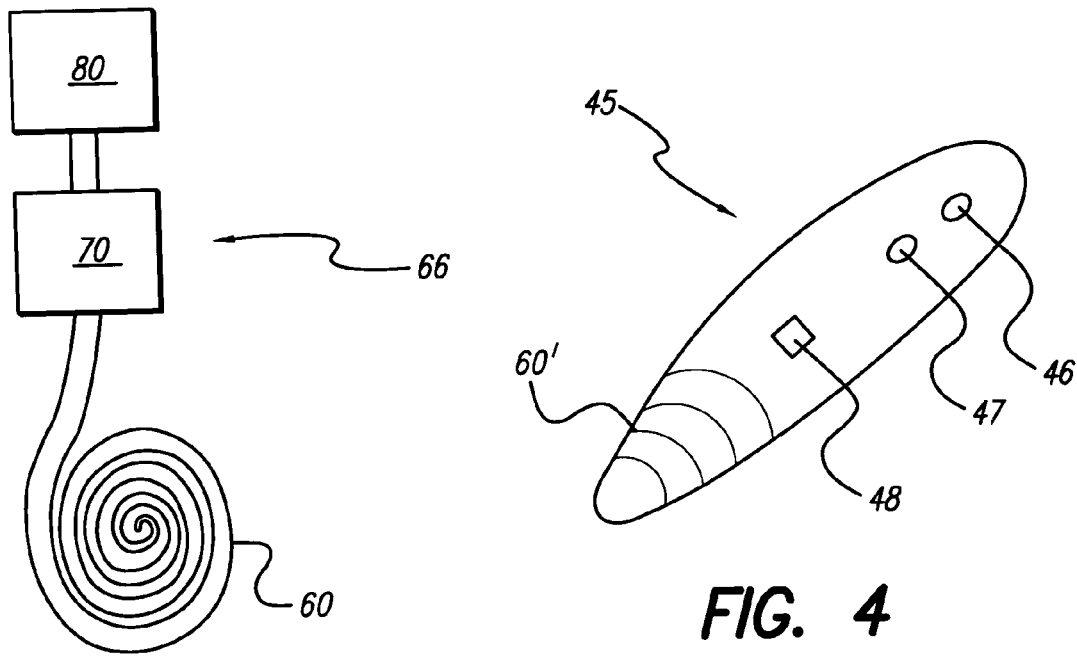
FIG. 3
FIG. 4
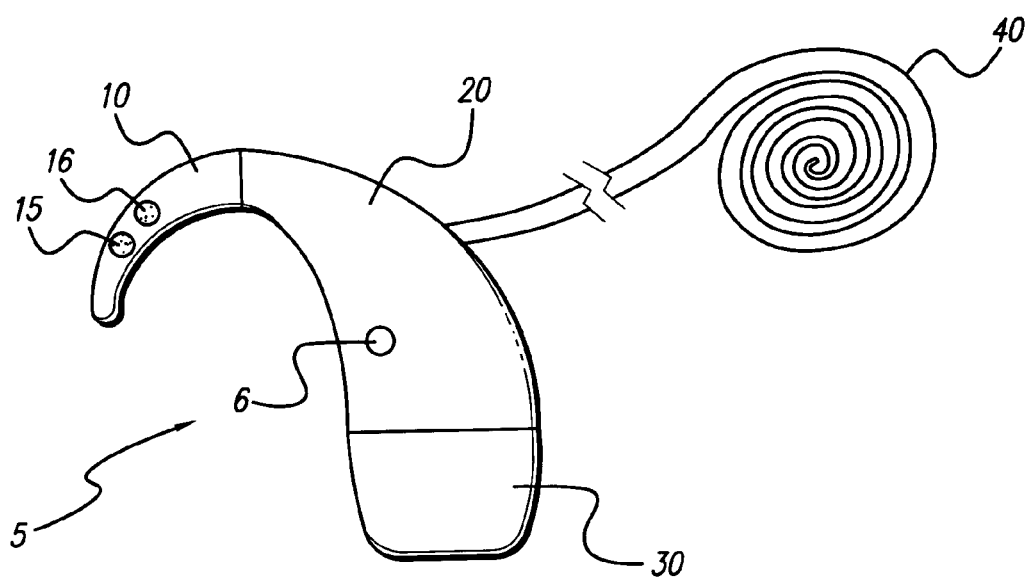
FIG 5

STATUS INDICATOR FOR IMPLANTABLE SYSTEMS

The present application claims the benefit of U.S. Provisional Application Serial No. 60/407,259, filed Aug. 30, 2002, which application is herein incorporated by reference in its entirety.

BACKGROUND OF THE INVENTION

The present invention relates to methods and devices for indicating the status of medical devices, including battery levels.

Medical devices are commonly powered by batteries and it is therefore important for the user to know if the batteries are running low. These devices may also have a number of functional modes and may selectably run a number of programs. It is desirable to have status (feedback) indicators to inform a care-giver or user concerning the device's current operating mode and program being run.

An implantable cochlear stimulator ("ICS") system can have two main components: an implantable ICS unit and an external behind-the-ear device ("BTE") which contains the system's battery. The details associated with the operation of a typical cochlear implant system may be found in one or more of the following U.S. patents, each of which is incorporated herein by reference in their entireties: U.S. Pat. Nos. 6,157,861; 6,002,966; 5,824,022; 5,603,726; 5,344,387; and 4,532,930.

The battery contained in the BTE unit, whether it is a one-time-use or a rechargeable variety, needs to be replaced or recharged periodically. An adult user knows when the battery becomes depleted because perceived sounds produced by the cochlear implant will become diminished or non-existent. Small children, however, are often unable to verbalize when the device is no longer functioning. In such pediatric use, it is important to have some external status indicator so that a parent or care-giver knows when the BTE battery needs to be replaced or recharged. Also, it would be beneficial to know when certain other operations and functions within a medical device are occurring. In particular, a conventional, ICS system uses a pair of magnetically coupled coils to transfer power and data signals transcutaneously between an external, transmitting coil that is attached to the BTE and an implanted receiving coil that is part of the implanted cochlear stimulator. When the patient is a child, it is important for a care-giver to know when there is a telemetry lock between the transmitting and implanted receiving coils so that the position of the headpiece containing the transmitting coil can be adjusted for best telemetry. In addition, there are other device functions such as activation of a selected BTE program among several programs, where it is useful for the care-giver and the user to know which program has been selected.

Accordingly, there is a need for a simple status indicator which can provide a care-giver or user the medical device's battery status, telemetry status or program selection.

SUMMARY OF THE INVENTION

The present invention addresses the above and other needs by providing devices and methods for obtaining battery status, telemetry status and program selection.

A cochlear stimulation system can include an external BTE device that is connected to a transmitting coil, which coil is used to inductively power an implanted receiving coil that delivers stimulation through stimulating electrodes. The transmitting coil may be powered by a primary or rechargeable battery in the BTE and produce alternating current through the transmitting coil. In an implantable, cochlear stimulator system, the alternating current in the transmitting coil can induce an alternating current in the implanted receiving coil.

The present invention is a status indicator that can detect current passing through the transmitting coil and thereby indicate battery status. When the primary or rechargeable battery powering the transmitting coil is good, an alternating current in the transmitting coil is used to inductively power a feedback element such as an LED in a separate receiving coil. Inductive coupling is accomplished by placing the status indicator containing the receiving coil very close to the transmitting coil. When current flows through the transmitting coil, the LED lights up, indicating that battery in the BTE is good.

In one aspect of the invention, a status indicating device or status indicator is provided which is comprised of a receiving coil and a feedback element. In one embodiment, the feedback element may be a visual indicator such as a light emitting diode ("LED"), which is electrically coupled in series to the receiving coil. In another embodiment, the status indicator can be in the form of a round, flat tab containing a receiving coil and an LED placed on the first surface of the tab and optionally, a sticky surface on the opposite surface of the tab. The sticky surface can have a level of stickiness that allows the tab to be temporarily attached over the housing of a transmitting coil connected to the BTE. The tab should be readily detachable once the test to detect current running through the transmitting coil is completed. The tab status indicator may then be thrown away.

In another embodiment, the status indicator may be built into a hand-held wand that has no separate power source but has a built in receiving coil and a feedback element such as an LED. It is emphasized that the feedback element draws its power from the induced current picked up by the receiving coil in the wand when current runs through the BTE transmitting coil.

In a further embodiment, the hand-held wand may include a battery, if additional power consuming functions such as a two-way, wireless communication is desired between the medical device (such as the BTE) or with an implanted medical device such as the implantable cochlear stimulator (ICS) portion of a cochlear stimulator system. Or a one-way receiving circuit may be used to detect when there is RE telemetry communication signals emanating from the BTE transmitting coil. It is emphasized, however, that the feedback element for detecting battery status may continue to be powered only by the induced current picked up by the receiving coil.

In another embodiment of the status indicator, the feedback indicator may be other than a simple LED. Instead, the feedback element may be a liquid crystal display (LCD), which may be electrically coupled to the receiving coil or the feedback element may be a sound producing device such as an acoustic speaker which may emit a short beep to indicate to a care-giver that a device's battery has adequate power. When the feedback element is an LCD or a sound producing device, it may be necessary to have additional electronic circuitry included in the status indicator device to rectify the alternating current in the receiving coil into a direct current in order to drive such a feedback element. For example, if the feedback element is a sound producing device such as a tiny speaker, it requires additional driving circuitry to produce sound from the speaker.

In operation, when the battery is good, alternating current will be produced at the transmitting coil which is part of the external medical device. For example, in cochlear stimulation, the external device may be a behind-the-ear device (BTE) that includes a one-time-only-use, primary battery or a rechargeable battery. If the battery is good or fully charged, alternating current will run through the BTE transmitting coil and this current may be detected with the status indicator device of the present invention.

A feature of the status indicator of the present invention is that the feedback element is not powered by a separate battery. Instead, all power to drive the feedback element and any other associated electronic circuitry of the status indicator may be drawn from the induced current picked up by the receiving coil when it is placed over the transmitting coil that is connected to the battery-powered medical device.

In yet another embodiment, the status indicator comprises a feedback element that is connected directly to the internal voltage supply of a BTE and no receiving coil is connected or used by the status indicator. The feedback element may be an LED which may illuminate to indicate that the battery level in the BTE is good. The LED may be placed on a detachable earhook, on the BTE or even on the battery portion of the BTE. Or, the feedback element may be a sound producing device.

Additional LEDs can be placed on the earhook or other portions of the BTE device to indicate other device functions such as whether there is sufficient telemetry between the transmitting coil connected to the BTE and the receiving coil that is implanted beneath the skin in the patient's head. The LEDs may also be used as visual indicators to immediately inform a care-giver, such as a parent or clinician, regarding other BTE functional or operational device modes. For instance, one or more LEDs may be used to indicate a specific program selection number, e.g., 1, 2 . . . N, by repetitively flashing the LED the exact number of times corresponding to the selected program number. Or an LCD feedback element may be used to directly display the program number. When LEDs or LCDs are fully integrated into the BTE, they can be linked to the electronic circuitry within the BTE and may draw power directly from the device's power supply.

It is thus a feature of the present invention to provide a status indicator for indicating battery level that can quickly and easily inform a care-giver, especially in the case when the patient is a child.

It is another feature of the present invention that, in one embodiment, the free-standing status indicator does not draw power from its own power source but draws power from the induced current generated in the receiving coil which is part of the status indicator.

It is yet another feature of the invention, in another embodiment, to have a battery status indicator that can be integrated directly into a BTE, with a feedback element that is attached to the headpiece, the BTE earhook, the BTE body or another component part of the BTE.

It is a further feature of the invention to provide a status indicator located on the medical device such as a BTE, which status indicator can provide additional information about a device's telemetry link, program selection or other device operating functions, in addition to battery level.

BRIEF DESCRIPTION OF THE DRAWINGS

The above and other aspects, features and advantages of the present invention will be more apparent from the following more particular description thereof, presented in conjunction with the following drawings wherein:

FIG. 1 shows an illustration of a conventional, cochlear stimulation system that includes the external BTE unit and implanted cochlear stimulator with a stimulating lead;

FIG. 2A shows, in accordance with the present invention, a diagrammatic illustration of a battery status indicator, employing a receiving coil and an LED feedback element;

FIG. 2B shows, in accordance with the present invention, an embodiment of the battery status indicator of FIG. 2A showing the LED feedback element placed on one surface of a tab that includes a receiving coil within the tab;

FIG. 3 shows, in accordance with the present invention, a diagrammatic illustration of an alternative embodiment of a status indicator having additional circuitry and a feedback element coupled to this circuitry;

FIG. 4 shows, in accordance with the present invention, an illustration of a hand-held wand incorporating one or more status indicators in the wand; and FIG. 5 shows, in accordance with the present invention, an illustration of an alternative embodiment of the present invention, wherein the status indicator is incorporated fully into a BTE hearing device.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

FIG. 1 shows an illustration of a conventional BTE unit 5 of a cochlear stimulation system. The device shows an exemplary BTE unit 5 having three separable pieces, an earhook 10, a main body 20 and a battery portion 30. The earhook 10 is detachable from the main body 20. Similarly, the battery portion 30 is also detachable from the main body 20. The battery contained in the battery portion 30 may be a rechargeable battery or it may be a primary, one-time-use-only, disposable battery. The BTE unit 5 is electrically coupled via an insulated, conductor 50 to a power transmitting coil/antenna 40 (which may be covered by a housing, or cover headpiece). Also shown is an implantable portion of the cochlear stimulator 25 that may be implanted beneath the skin in the patient's head. The housing of ICS 25 contains an implanted receiving coil (not shown). A cochlear stimulating lead 28 can be connected to the ICS 25 which lead has a multiplicity of electrode contacts 27 that are used to stimulate the ganglion nerves inside the patient's cochlea.

The transmitting coil 40 can be placed over an implantable portion of the cochlear stimulator (ICS) 25 which contains the implanted receiving coil. The ICS implanted receiving coil can accept data signals and RF power from the power transmitting coil 40 as well as send back signals via the transmitting coil as signified by the arrows 29. The transferred RF power in the ICS 25 can be rectified and used to drive a multiplicity of stimulation channels to deliver stimuli through the electrode contacts 27.

FIG. 2A shows, in accordance with the present invention, a diagrammatic illustration of a battery status indicator 65, comprising a receiving coil 60 and a feedback element 81. In the simplest form, the feedback element 81 may be a visual indicator such as an LED. The coil 60 can be covered with a protective, insulating material and the feedback element 81, such as an LED, can be optionally attached to the top of the coil 60. The battery status indicator 65 can be advantageously small and self-contained.

The size of the receiving coil 60 may be substantially smaller than the transmitting coil 40 depending on the power requirement of the feedback element 81. The number of turns in the receiving coil 60 may also be less than in the transmitting coil 40. Although a flat receiving coil 60 is preferred, the coil may be configured to other shapes known in the art.

FIG. 2B shows one embodiment of the status indicator of FIG. 2A. The status indicator is a flat tab 65' which includes within it a multiple turn coil 60' that is connected in series to a small LED 81' attached to a first surface of the tab. The coil 60' may be sandwiched inside two thin sheets of material such as paper or a polymer. The tab shown is shaped as a circle, although other shapes may suffice as long as there is sufficient surface area for the coil 60' to operate. The second surface of the tab may optionally be coated with an adhesive having a level of stickiness that allows the tab to be temporarily attached over a housing of a BTE transmitting coil and then removed.

To check the battery status of the BTE 5, the status indicator 65' is attached directly over the housing (head-piece) of a BTE transmitting coil 40. When the battery power level is sufficient, alternating current will flow through the transmitting coil 40. An induced alternating current will flow through the receiving coil 60'. This induced alternating current can light up the visual feedback element, LED 81', thereby signaling to the user that the BTE battery is good. After the battery test is performed, the tab 65' can be discarded, as it is relatively inexpensive. This visual indicator is particularly useful in case the user is a small child who cannot verbalize his or her perceptions, as a parent or care-giver can immediately see the status of the BTE battery and therefore take appropriate action.

FIG. 3 shows, in accordance with the present invention, a diagrammatic illustration of an alternative embodiment of status a indicator 66, having additional circuitry 70 and feedback element 80 coupled to this circuitry. Instead of an LED, the feedback element 80 may be a different type of visual display such as a liquid crystal display (LCD) or it may be, instead, a sound producing device such as an audio speaker. Such feedback elements 80 can require additional driving circuitry 70. Induced, alternating current picked up in the receiving coil 60 may be used to drive the circuitry 70 and the feedback element 80 and hence no separate source of battery power in the status indicator is required. The status indicator depicted in FIG. 3 may also be made into a tab form such as depicted in FIG. 2B. In that case, the feedback element 80 and additional circuitry 70 may be placed on a first surface of the tab and second tab surface may optionally have an adhesive surface.

FIG. 4 shows, in accordance with the invention, another possible form of a free-standing status indicator, in the form of a hand-held wand. The wand 45 can incorporate the status indicators of FIG. 2A or FIG. 3. In the simplest embodiment, the wand may have only a single LED 46. It is emphasize that when feedback element 46 or 47 on the wand is used to indicate battery status, it may be powered inductively. The feedback element 46 or 47 may be a visual feedback element such as an LED or LCD, or it may be a sound producing device. A power receiving coil 60' may be in a form that is flat or it may be another shape and configuration known in the art.

To check the battery status, the wand 45 is brought very close to the transmitting coil 40 (shown in FIG. 1). The LED 46 should automatically illuminate or an audio speaker 47 will produced a sound, if alternating current is detected in the transmitting coil 40, as induced current will be picked up in coil 60'. The sounds or emitted light will terminate when the wand 45 is taken away from the transmitting coil 40 because induced current to the receiving coil will cease to flow. Or no sounds or light will be produced when the BTE battery level is low.

In a more sophisticated embodiment of the wand, the wand may include a battery as well as additional circuitry. The first LED 46 may still function as a battery status indicator in the manner previously described. The additional circuitry, however, enables the wand/status indicator to perform more complex functions in addition to detecting battery status. For example, the wand may act as an RF sniffer to detect RF telemetry emanating from the transmitting coil/antenna 40. The second LED 47 or another LED on the wand may be used to check whether there is RF telemetry emitted from the BTE. Morever, the wand may contain electronic circuitry that enables two-way, wireless, bidirectional RF communication with the BTE. Other functions which may be checked include identification of the selected program among several possible BTE programs. With the wand held up to several feet or more away from the BTE transmitting coil 40, a switch 48 can be pressed to indicate the program selection. If an LED is used, it may flash the exact number of the selected program. For example, selection of program 3 would be indicated by flashing the LED three times. If an LCD is used, the number three can be directly displayed as the number itself.

FIG. 5 shows, alternatively, another embodiment wherein the status indicator is fully incorporated into the BTE 5. In such a case, no receiving coil is used. The feedback element 15 or 16 is placed on the BTE 5 and is directly connected either to the voltage source or connected in series with the transmitting coil 40. Feedback elements such as an LED or an LCD may be placed on various parts of the BTE such as on the earhook 10, the body 20, the battery portion 30 or even the transmitting coil 40. The main requirement is that when a visual feedback element is used, that it be readily and quickly visible to care-givers, including clinicians and parents.

The feedback element 15 or 16 may be a sound producing device such as an audio speaker. Additional electronic circuitry may be necessary to drive the speaker including a rectifying circuit and an amplifier. These elements are preferably miniaturized to take up the least amount of space. When the battery status indicator is built into the BTE 5, an optional external switch 6, as shown in FIG. 4, may be used. The switch 6 may be pressed on to enable the audio speaker to produce sounds such as intermittent beeps, indicating to the care giver or clinician that current is running through the transmitting coil 40.

A plurality of LEDs having different colors can be placed on the BTE and used to indicate different functions. However, as more LEDs are used, more battery power will be drawn. At least one of the LEDs should flash or illuminate to indicate that the battery is good. Another LED may be used to indicate when the telemetry is locked.

Another use of the LEDs 15 or 16 is to provide status indication on which program number among several programs is activated within the BTE. Each program selection should have an associated whole number 1, 2, 3 . . . N. An LED 15 or 16 can be used to convey the program selection by repetitively flashing the exact number of times corresponding to the program number selected. The LEDs may flash continuously or they may flash only when queried. If an LCD is used, it may be flashed or, more preferably, it may display the actual program number.

Thus, in summary, in one aspect of the invention, a free-standing status indicator is disclosed having a receiving coil and a feedback element which is coupled to the receiving coil, wherein the status indicator is inductively powered. In one embodiment, the status indicator may be in the form of a tab or may be incorporated into a hand-held wand. The feedback element may be, in the simplest form, a visual feedback element such as an LED. Alternatively, with inclusion of additional circuitry coupled to the receiving coil, the feedback element can be an LCD or an audio speaker.

In another aspect of the invention, the status indicator can be fully incorporated into the medical device, such as a BTE, and provide not only battery status, but device function and program selection.

In still another aspect of the invention, a method is provided for detecting battery status in a medical device employing a transmitting coil, the method comprising: (a) placing a receiving coil over the medical device transmitting coil and (b) detecting the induced current in the receiving coil with a feedback element.

While the invention herein disclosed has been described by means of specific embodiments and applications thereof, numerous modifications and variations could be made thereto by those skilled in the art without departing from the scope of the invention set forth in the claims.

What is claimed is:

1. A stick-on status indicator for use with a cochlear implant system, the cochlear implant system including a headpiece wherein a transmitting coil is housed, and wherein the transmitting coil is used to transcutaneously power an implantable pulse generator (IPG) that is part of the cochlear implant system, wherein the status indicator consists of the following electrical components:
   a receiving coil, and
   a light emitting diode (LED) electrically connected in series with the receiving coil; and
   wherein induced current is generated in the receiving coil by inductive coupling with the transmitting coil when the transmitting coil has alternating current flowing through it; and
   wherein the LED is powered on by the induced current generated in the receiving coil; and
   wherein the receiving coil and LED are affixed to a flat tab having a shape and size adapted to fit over and be detachably secured to an outer surface of the headpiece.

2. The stick-on status indicator of claim 1 wherein the flat tab comprises two thin sheets of a first material, and wherein the receiving coil and LED are sandwiched inside the two thin sheets of material.

3. The stick-on status indicator of claim 2 wherein the tab has the shape of a circle.

4. The stick-on status indicator of claim 3 wherein an outer surface of one of the two thin sheets of material is coated with an adhesive having a level of stickiness that allows the tab to be detachably secured to the outer surface of the headpiece.

5. A hand-held status indicator for use with a cochlear implant system, the cochlear implant system including a headpiece wherein a transmitting coil is housed, and wherein the transmitting coil is used to transcutaneously power an implantable pulse generator (IPG) that is part of the cochlear implant system, wherein the status indicator consists of the following electrical components:
   a receiving coil, and
   a light emitting diode (LED) electrically connected in series with the receiving coil; and
   wherein induced current is generated in the receiving coil by inductive coupling with the transmitting coil when the transmitting coil has current flowing through it; and
   wherein the LED is powered on by the induced current generated in the receiving coil; and
   wherein the receiving coil and LED are housed within a hand-held wand that is separate and apart from the cochlear implant system; and
   wherein the LED is powered on by induced current generated in the receiving coil whenever the hand-held wand is held near the headpiece.

6. A method for detecting battery status of an external battery used with a cochlear implant system, the cochlear implant system including an external sound processor having the external battery, a headpiece having a transmitting coil connected to the external sound processor, wherein the transmitting coil is used to transcutaneously transfer power from the external battery to an implantable pulse generator (IPG) that is part of the cochlear implant system, wherein the method for detecting battery status comprises:
   assembling a status indicator, separate and apart from the cochlear implant system, that electrically consists of only the following electrical components:
      a receiving coil, and
      a light emitting diode (LED) electrically connected in series with the receiving coil;
   positioning the status indicator so that the receiving coil of the status indicator is physically close to the transmitting coil in the headpiece; and
   detecting electrical current induced in the receiving coil by observing whether the LED in the status indicator is powered on, a powered on condition of the LED indicating that electrical current has been induced in the receiving coil from the power being transferred from the external battery through the transmitting coil to the implantable pulse generator, and hence a powered on condition of the LED indicating that functioning properly.

* * * * *